United States Patent [19]

Correia

[11] Patent Number: 4,659,513

[45] Date of Patent: Apr. 21, 1987

[54] DISPROPORTIONATION OF UNSATURATED ACIDS IN ROSIN OR TALL OIL

[75] Inventor: Joao M. G. Correia, Lisbon, Portugal

[73] Assignee: Enichem Elastomers Limited, Hardley, United Kingdom

[21] Appl. No.: 836,993

[22] Filed: Mar. 6, 1986

[30] Foreign Application Priority Data

Mar. 8, 1985 [GB] United Kingdom ............... 8506023

[51] Int. Cl.$^4$ ............................................... C09F 1/00
[52] U.S. Cl. ...................................... 260/97; 260/98; 260/99.5
[58] Field of Search ........................... 260/97, 98, 99.5

[56] References Cited

U.S. PATENT DOCUMENTS 4,481,145 11/1984 Timms ................................... 260/97

FOREIGN PATENT DOCUMENTS 1021757 3/1966 United Kingdom ................. 260/97

*Primary Examiner*—Herbert S. Cockeram
*Attorney, Agent, or Firm*—Cushman, Darby & Cushman

[57] ABSTRACT

The process relates to a method of improving the color and/or reducing the oxidized acids content of the disproportionated product obtained by heating rosin acids in rosin and tall oil with a catalyst comprising iodine, an iron compound and ammonia, an ammonium salt or an amine. The improvement comprises a pretreatment step in which the starting material is heated with an effective amount not in excess of 0.5% by weight of elemental sulphur, based on the weight of starting material for a period, usually less than one hour. As little as 0.1% by weight of sulphur is sufficient in most cases.

6 Claims, No Drawings

DISPROPORTIONATION OF UNSATURATED ACIDS IN ROSIN OR TALL OIL

This invention relates to a process for the disproportionation of unsaturated acids in rosin or tall oil. However the invention relates not so much to the disproportionation step itself but to a method of improving the colour of the product obtained by a particular and very effective disproportionation process as disclosed and claimed in our British patent specification No. 2113686 (and also U.S. Pat. No. 4,481,145).

Raw rosin consists of about 90% or more of mixed unsaturated acids. These are mainly isomeric rosin acids but in some cases, such as in tall oil rosin, a considerable proportion of fatty acids, mainly oleic and linoleic acid, is present as well. The isomeric rosin acids are of general formula $C_{19}H_{29}$ COOH and comprise abietictype acids, pimaric-type acids, dihydroabietic acid and tetrahydroabietic acid. The chemistry of rosin (and rosin derivatives) is therefore quite complex. Modification of rosin is very desirable and there is an abundance of literature describing suitable methods, extending back over at least fifty years. For example, U.S. Pat. No. 1,957,788 (1934) describes a method of refining or lightening the colour of rosin by treatment with a halogen, indicating the importance of colour even in the early days of rosin technology.

Disproportionation is a preferred method of modifying rosin on a commercial scale. Disproportionation is a term used to describe the removal of conjugated dienic groups from the rosin molecules. In the disproportionation reaction, the abietic acids (which have conjugated double bonds) are converted to di- and tetrahydroabietic acid and dehydroabietic acids. The reaction is of particular importance in the manufacture of soaps suitable for emulsion polymerisation processes (e.g. styrene-butadiene rubber manufacture) since it has long been known that the conjugated double bonds in the raw rosin interfere with the polymerisation reaction.

A wide variety of catalysts is known to catalyse the disproportionation reaction. In our British patent specification No. 2113686 (U.S. Pat. No. 4,481,145) we have claimed a specific and very effective method of disproportionation comprising heating the rosin or tall oil with a three component catalyst comprising iodine, an iron salt and ammonia, an ammonium salt or an amine. The rosin or rosin containing material is simply heated with the three component catalyst until the abietic acid content is reduced to the desired level, usually less than 1% by weight. Typically the reaction is carried out at a temperature of 190° to 220° C. and, under these conditions, it appears to be highly selective since hydrogenated and dehydrogenated products approximately balance.

An important criterion of rosin quality is the colour which is represented on a scale by comparison with colour standards as described in ASTM D509/70. Raw untreated rosin varies considerably in colour and in content of so-called "oxidized acids" which are insoluble in paraffinic hydrocarbons. The disproportionation process claimed in our above mentioned British patent specification effects some improvement in colour but does not always reduce the content of oxidized acids to an acceptable level.

According to the present invention an improvement in the said disproportionation process comprises pretreatment of the starting material by heating with an effective amount not in excess of 0.5% by weight of elemental sulphur, based on the weight of starting material whereby to improve the colour and/or reduce the oxidised acid content of the disproportionated product.

The temperature used for the pretreatment step is quite critical and is preferably 250° to 270° C., more preferably 260° to 265° C. Below 250° C. the bleaching action and removal of oxidised acids is less effective whilst above 270° C. there is the risk of decarboxylation of the rosin acids, as is well known in the disproportionation art. The time used for the pretreatment is usually less than one hour and a period of about 30 minutes is quite sufficient in most cases.

As will be discussed below, the use of sulphur, usually in conjunction with alcohol or alkali, to disproportionate rosin is known but it is important to distinguish the use of the quite large amounts of sulphur disclosed as reaction catalysts in the prior art from use of the absolutely minimum effective amount, normally about 0.1% by weight, of sulphur in the pretreatment process of the present invention to improve product colour in the subsequent specific disproportionation reaction which does not use sulphur at all. This is especially desirable because of the environmental problems associated with hydrogen sulphide/sulfur dioxide emissions which are common when sulphur is used in large quantities as a disproportionation catalyst.

U.S. Pat. No. 2,407,248 (Hercules Powder Co.) claims a method of stabilising a material selected from polymerised rosin and polymerised rosin esters, which comprises heating the material for at least three hours with from about one to about ten percent of sulfur based upon the weight of said material, at a temperature between about 150° and about 350° C. until the bromine number of the material has become reduced to below about 75 without a decrease in its melting point. The reaction conditions are such as to effect substantial dehydrogenation of the rosin or rosin ester and yields a new and distinct product.

U.S. Pat. No. 2,409,173 (Ridbo Laboratories Inc.) claims in the production of a rosin ester of low unsaturation from rosin of high unsaturation, the process for concurrently effecting esterification and reduction of unsaturation, which process consists in heating the rosin to a temperature between about 150° C. and 300° C. and subjecting the heated rosin concurrently to the action of an alcohol and of from 0.5% to 25% by weight of the rosin of sulfur, the temperature and time of heating being sufficient to effect esterification and reduction of unsaturation. Reaction times of eight hours or more are shown in the examples.

U.S. Pat. No. 2,497,882 (The Glidden Company) claims a process of producing an improved rosin composition characterised by imparting an increased resistance to yellowing in soaps and sizes made therefrom, which process consists of heating a rosin material under non-oxidising conditions with from 0.5% to 5% in sulfur equivalent, of at least one catalytic material selected from the group consisting of sulfur, sulfur halides, alkali metal sulfides and alkali metal polysulfides, in the presence of a small percentage up to about 38% of the stoichiometric quantity of an alkali metal alkali required to neutralise the rosin material, at a temperature between about 200° C. and 375° C. for a time sufficient to decrease the degree of unsaturation without aromatization of substantially more than one ring of the rosin material. A time period of one to three hours at a temperature of around 275° C. is generally satisfactory with sulfur concentrations of about 1% to 3%.

British Pat. No. 1,021,757 (Granel Freres) describes the disproportionation of natural resins by successively heating the resin, first of all with a catalytic amount of sulphur and then adding a catalytic amount of iodine and continuing the heating until the desired content of dehydroabietic acid is obtained. It is to be particularly noted that the first stage in the presence of sulphur as catalyst is carried out until there is obtained a substantial content of dehydroabietic acid and the amount of sulphur used is preferably one to 10% by weight of sulphur or better still 2 to 5% and the temperature is between about 180° and 250° C. Usually the heating period with each catalyst is between 1 and 5 hours.

In U.K. Pat. No. 1,251,924 (Arizona Chemical Co.) at lines 30 to 50 there is an acknowledgement of prior art processes: "It is known in the art that rosin can be disproportionated by heating it at elevated temperature in the presence of catalysts. Typically U.S. Pat. No. 3,277,072 teaches the use of iodine, while other prior art teaches the use of noble metals, such as platinum or palladium. The use of sulfur or selenium is also suggested in the prior art. These treatments, however, result only in disproportionation. The treated rosin not only is not bleached, but may actually darken as the result of heating for prolonged periods at high temperatures."

As is clear from the above discussion, the amount of sulphur required in the present invention to effect the improvement in colour is very small, normally 0.1 to 0.5% maximum, on a weight/weight basis. For example 0.1% weight/weight effects considerable colour improvement and reduction in oxidised acid content. 0.1% is however to be regarded as a practical guideline and quantities of sulphur greater or less than 0.1% by weight may be employed, the exact amount chosen depending on the quality of the starting material and the degree of improvement in colour desired. Furthermore the small amount of sulphur is the only additive employed, the pretreatment step not involving alcohol (as required by U.S. Pat. No. 2,409,173) or alkali (as required by U.S. Pat. No. 2,497,882) which in any case are directed at the problem of disproportionation itself not at the problem of improving colour and oxidised acid content in the process of our aforementioned British patent.

In contrast to the processes of these prior art references the process of the present invention is not a disproportionation process but is a pretreatment process using only as small an amount of sulphur as possible to improve the colour of the product obtained by the disproportionation process of our U.K. Pat. No. 2113686. That the pretreatment step is effective to improve colour in this way is particularly surprising bearing in mind the above quoted passage from U.K. Pat. No. 1,251,924 considering also that a characteristic feature of the pretreatment step is that no significant disproportionation is obtained by the pretreatment step on its own.

This invention is now illustrated by the following Example:

EXAMPLE 500g of grade WG rosin were placed in a 700 ml glass reaction vessel equipped with stirrer and gas purging facilities. The rosin was heated with stirring under nitrogen to 255° C. then 0.5g (i.e. 0.1% w/w) sulphur was added and heat was applied to raise the temperature to 265° C. The melt was held at this temperature for 30 minutes during which time a very small amount of hydrogen sulphide was liberated along with some terpene oil.

After this pretreatment the melt was cooled to 150° C. then 0.10g ferric chloride hexahydrate, 0.10g urea and 2.0 g flake iodine were added in that order. The mixture was heated to 210° C. for 2 hours then cooled to 160° C. and treated with 3.0 g hydrated oxalic acid. The product was rated colour X and the 10% solution in hexane was only faintly opalescent. The abietic acid content was 0.3% as determined by UV analysis.

Without the pretreatment with sulphur step the colour was darker, varying from WG to WW. The solution in hexane varied from slightly cloudy to cloudy with formation of a flocculent precipitate.

The starting material gave a dense precipitate when dissolved in hexane.

The colours mentioned above are based on the conventional U.S. Department of Agriculture (USA Naval stores/ASTM D509 scale consisting of interalia (and in order of colour lightness), X, WW, WG, N etc.

It can thus be seen that the pretreatment process using 0.1% weight/weight of elemental sulphur effects a significant improvement in colour and reduces the oxidised acid content of the disproportionated product to a very low level.

On the other hand the pretreatment step alone produced virtually no significant disproportionation.

What we claim is:

1. An improvement in a process for disproportionating unsaturated acids in rosin or tall oil by heating with a catalyst comprising iodine, an iron compound and ammonia, an ammonium salt, urea or an amine, the improvement comprising a pretreatment step of heating the starting material with an effective amount not in excess of 0.5% by weight of elemental sulphur, based on the weight of starting material, whereby to improve the colour and/or to reduce the oxidised acid content of the final disproportionated product with no significant disproportionation during the pretreatment step.

2. The improvement according to claim 1 in which a temperature of 250° C. to 270° C. is used for the pretreatment step.

3. The improvement according to claim 1 in which the time for the pretreatment is less than one hour.

4. The improvement according to claim 1 in which the amount of sulphur used is substantially 0.1%.

5. The improvement according to claim 2 in which the amount of sulphur used is substantially 0.1% by weight and the time for the pretreatment is less than one hour.

6. The improvement according to claim 5 in which the time for the pretreatment is substantially 30 minutes.

* * * * *